United States Patent [19]
Romano et al.

[11] Patent Number: 5,795,336
[45] Date of Patent: Aug. 18, 1998

[54] AUTOMATIC NEEDLE PROTECTOR HAVING FEATURES FOR FACILITATING ASSEMBLY

[75] Inventors: John F. Romano, Washington Crossing; William Patrick McVay, Doylestown, both of Pa.; Larry M. D'Alessio, Manasquan, N.J.

[73] Assignee: Beech Medical Products, Inc., Middlesex, N.J.

[21] Appl. No.: 850,338

[22] Filed: May 2, 1997

Related U.S. Application Data

[63] Continuation of Ser. No. 387,676, Feb. 13, 1995, abandoned, which is a continuation-in-part of Ser. No. 159,053, Nov. 29, 1993, Pat. No. 5,389,085, which is a continuation-in-part of Ser. No. 16,285, Feb. 11, 1993, Pat. No. 5,292,314.

[51] Int. Cl.$^6$ ...................................................... A61B 5/14
[52] U.S. Cl. .................. 604/192; 604/110; 604/198; 604/263; 604/197
[58] Field of Search ............................... 604/110, 192, 604/198, 263, 197

[56] References Cited

U.S. PATENT DOCUMENTS

| | | | |
|---|---|---|---|
| 670,018 | 3/1901 | Groth | 604/198 |
| 3,134,380 | 5/1964 | Armao | 128/215 |
| 3,727,613 | 4/1973 | Sorenson et al. | 128/214.4 |
| 3,859,998 | 1/1975 | Thomas et al. | 128/214.4 |
| 3,865,236 | 2/1975 | Rycroft | 206/364 |
| 4,178,730 | 12/1979 | Fisher, Jr. | 128/215 |
| 4,178,930 | 12/1979 | Fisher, Jr. | 128/215 |
| 4,205,675 | 6/1980 | Vaillancourt | 128/214.4 |
| 4,205,767 | 6/1980 | Shackelford | 222/542 |
| 4,232,669 | 11/1980 | Nitshke | 128/218 N |
| 4,237,882 | 12/1980 | Wickham | 128/218 N |
| 4,329,989 | 5/1982 | Dallons et al. | 128/218 R |
| 4,392,859 | 7/1983 | Dent | 604/198 |
| 4,507,118 | 3/1985 | Dent | 604/198 |

(List continued on next page.)

OTHER PUBLICATIONS

*Interlink®* I.V. Access System product literature, Baxter Healthcare Corporation, 1993, sixteen pages.
*Pro-Lok*™ Shielded Needle Connector Assembly product literature, Beech Medical Products, Inc., six pages.
*Pro-Lok*™ product literatue, Beech Medical Products, Inc., two pages.
*Versa-Lok*™ product literature, Beech Medical Products, Inc., two pages.
*Corporate Experience Bolsters Small Firm in Big Ways*, D. Jefferson, Wall Street Journal, one page.

(List continued on next page.)

Primary Examiner—Aaron J. Lewis
Assistant Examiner—Charles W. Anderson
Attorney, Agent, or Firm—Judith C. Crowley; Nutter, McClennen & Fish LLP

[57] ABSTRACT

A needle protector device including a mount having a needle subassembly attached to an upper end, an open lower end, and an aperture in the side of the mount. The aperture includes an entrance position adjacent to the lower end of the mount and an armed position radially spaced from the entrance position by an angled portion of the mount. A protective cover is coupled to the mount and has a protruding lug which engages the mount aperture. The cover is adapted for being a needle protection position in which the needle tip is covered and the cover is not retractable, an armed position in which the needle tip is covered and the cover is retractable, and a retracted position in which the needle tip extends through an open lower end of the cover. A spring having a pair of axial extensions is coupled between the mount and the cover. The spring is biased in rotation and compression during assembly of the device, causing the cover to be automatically urged to the needle protection position. The needle subassembly is press fit into the mount and the mount includes an assembly ramp for accommodating the cover lug during assembly.

20 Claims, 9 Drawing Sheets

U.S. PATENT DOCUMENTS

| | | | |
|---|---|---|---|
| 4,511,359 | 4/1985 | Vaillancourt | 604/411 |
| 4,564,054 | 1/1986 | Gustavsson | 141/329 |
| 4,578,061 | 3/1986 | Lemelson | 604/164 |
| 4,610,667 | 9/1986 | Pedicano et al. | 604/192 |
| 4,615,331 | 10/1986 | Kramann | 128/4 |
| 4,619,644 | 10/1986 | Scott | 604/53 |
| 4,623,336 | 11/1986 | Pedicano et al. | 604/192 |
| 4,627,841 | 12/1986 | Dorr | 604/158 |
| 4,643,199 | 2/1987 | Jennings, Jr. et al. | 128/763 |
| 4,652,256 | 3/1987 | Vaillancourt | 604/52 |
| 4,654,034 | 3/1987 | Masters et al. | 604/192 |
| 4,659,330 | 4/1987 | Nelson et al. | 604/192 |
| 4,664,654 | 5/1987 | Strauss | 604/198 |
| 4,675,005 | 6/1987 | DeLuccia | 604/110 |
| 4,676,783 | 6/1987 | Jagger et al. | 604/171 |
| 4,681,567 | 7/1987 | Masters et al. | 604/198 |
| 4,693,708 | 9/1987 | Wanderer et al. | 604/192 |
| 4,702,738 | 10/1987 | Spencer | 604/198 |
| 4,723,942 | 2/1988 | Scott | 604/164 |
| 4,723,943 | 2/1988 | Spencer | 604/198 |
| 4,725,267 | 2/1988 | Vaillancourt | 604/192 |
| 4,731,059 | 3/1988 | Wanderer et al. | 604/192 |
| 4,735,618 | 4/1988 | Hagen | 604/192 |
| 4,737,144 | 4/1988 | Choksi | 604/192 |
| 4,740,204 | 4/1988 | Masters et al. | 604/192 |
| 4,747,830 | 5/1988 | Gloyer et al. | 604/110 |
| 4,747,831 | 5/1988 | Kulli | 604/110 |
| 4,747,837 | 5/1988 | Hauck | 604/198 |
| 4,762,516 | 8/1988 | Luther et al. | 604/164 |
| 4,772,272 | 9/1988 | McFarland | 604/198 |
| 4,775,369 | 10/1988 | Schwartz | 604/263 |
| 4,778,453 | 10/1988 | Lopez | 604/110 |
| 4,781,697 | 11/1988 | Slaughter | 604/192 |
| 4,782,841 | 11/1988 | Lopez | 128/164 |
| 4,790,827 | 12/1988 | Haber et al. | 604/198 |
| 4,790,828 | 12/1988 | Dombrowski et al. | 604/198 |
| 4,795,432 | 1/1989 | Karczmer | 604/110 |
| 4,795,443 | 1/1989 | Permenter et al. | 604/198 |
| 4,801,295 | 1/1989 | Spencer | 604/198 |
| 4,832,696 | 5/1989 | Luther et al. | 604/164 |
| 4,834,716 | 5/1989 | Ogle, II | 604/192 |
| 4,846,809 | 7/1989 | Sims | 604/198 |
| 4,894,055 | 1/1990 | Sudnak | 604/198 |
| 4,911,693 | 3/1990 | Paris | 604/192 |
| 4,911,706 | 3/1990 | Levitt | 604/198 |
| 4,923,447 | 5/1990 | Morgan | 604/198 |
| 4,932,940 | 6/1990 | Walker et al. | 604/110 |
| 4,955,866 | 9/1990 | Corey | 604/192 |
| 4,978,344 | 12/1990 | Dombrowski et al. | 604/198 |
| 4,994,034 | 2/1991 | Botich et al. | 604/110 |
| 4,994,041 | 2/1991 | Dombrowski et al. | 604/164 |
| 5,049,136 | 9/1991 | Johnson | 604/198 |
| 5,092,851 | 3/1992 | Ragner | 604/192 |
| 5,104,384 | 4/1992 | Parry | 604/192 |
| 5,114,409 | 5/1992 | Kole et al. | 604/192 |
| 5,120,324 | 6/1992 | Sancoff | 604/283 |
| 5,122,123 | 6/1992 | Vaillancourt | 604/192 |
| 5,139,483 | 8/1992 | Ryan | 604/86 |
| 5,169,392 | 12/1992 | Ranford et al. | 604/198 |
| 5,188,599 | 2/1993 | Botich et al. | 604/110 |
| 5,195,983 | 3/1993 | Boese | 604/192 |
| 5,201,708 | 4/1993 | Martin | 604/110 |
| 5,207,667 | 5/1993 | Walder et al. | 604/905 |
| 5,279,583 | 1/1994 | Shober, Jr. et al. | 604/198 |
| 5,290,256 | 3/1994 | Weatherford et al. | 604/198 |
| 5,312,371 | 5/1994 | Dombrowski et al. | 604/198 |
| 5,376,073 | 12/1994 | Graves et al. | 604/86 |
| 5,389,085 | 2/1995 | D'Alessio et al. | 604/198 |
| 5,407,431 | 4/1995 | Botich et al. | 604/110 |
| 5,607,392 | 3/1997 | Kanner | 604/86 |

OTHER PUBLICATIONS

*Stick–Gard™ Safety Needle*, product literature, International Medication Systems, Limited, Sep. 18, 1989, two pages.

*Burron Medical Safsite™, ICU Medical Click Lock™ and IMS Stick–Gard™*, ECRI, Special Report and Product Review, Health Devices, vol. 20, No. 5, May 1991, pp. 165–166.

*ICU Medical Inc. Click Lock and International Medication Systems (IMS) Ltd. Stick–Gard*, ECRI, Evaluation Updates, Health Devices, vol. 20, No. 12, Dec. 1991, one page.

*Intravenous Medication Connectors*, ECRI., Oct. 1992, one page.

*Becton Dickinson (B–D) Safety–Gard IV Needle*, ECRI, Health Devices, vol. 23, No. 8–9, Aug./Sep. 1994, one page.

AUTOMATIC NEEDLE PROTECTOR HAVING FEATURES FOR FACILITATING ASSEMBLY

RELATED CASE INFORMATION

This application is a file wrapper continuation of application Ser. No. 08/1387,676 filed Feb. 13, 1995, now abandoned, which is a continuation-in-part of U.S. patent application Ser. No. 08/159,053 filed Nov. 29, 1993 which issued as U.S. Pat. No. 5,389,085, entitled: AUTOMATIC NEEDLE PROTECTOR, on Feb. 14, 1995, which is a continuation-in-part of Ser. No. 016285, filed Feb. 11, 1993, now U.S. Pat. No. 5,292,314.

FIELD OF THE INVENTION

This invention relates generally to needle protection devices and, more specifically, to needle protection devices providing automatic needle protection with re-arming capability and features for facilitating assembly.

BACKGROUND OF THE INVENTION

The use of needles for penetrating the body is essential in modern medicine. Their uses include injecting fluids into, or drawing blood or other fluids out of almost any part of the body. The sizes of the needles, and the associated syringe equipment, will vary according to their function.

However, regardless of the size, use, or function, the needle is inevitably a sharp and potentially hazardous object. It should be safely stored, and, more important, safely discarded after any use. This is mandatory at all health facilities, but the facts prove that, with human nature, and overworked, human hospital staffs, used needles will always be found, and will always be a potential hazard.

The potential danger in needles is, of course, in used needles that may have picked up a virus of some kind from anyone using, or being injected by a needle. Once used, the needle must be considered contaminated, and, even if the risk is microscopic, it is a potential threat to the next person who, accidentally or otherwise, comes in contact with the needle. With certain deadly viruses living in a few human beings today, no gamble, however microscopic, is tolerable.

All hospitals, and other users of needles, have established systems and rules for the control of the use of and disposition of needles. Most of these are almost foolproof, and restrict the use of needles to well trained professional personnel. However, it is now these, valuable people who are at risk from the casual, unprotected needle that may have been accidentally overlooked, and just lying around. Contact with this needle could be equally unpredictable. One could be standing, sitting, or in motion of any kind, and the contact could be with any part of the body.

Again, the risk of a trained medical technician coming in contact with a stray needle—let alone its sharp end—should be negligible, and, that this particular needle might be infected, would be another very-remote possibility, but, where that possibility, however remote, could be lethal, or harmful in any way, the stakes are still too high.

The obvious, and basic, solution to the problem would be to have a safety shield or cover over the needle, before and after it is used. This is done quite effectively in several of the systems, but, in most of the systems, it relies on the human function of putting on, taking off, and putting the safety shield back on before discarding the needle in the required manner.

What is needed is a safety shield that is part of the needle structure, and that is locked in a position that covers and protects the sharp end of the needle. There must be a means for uncovering the safety shield, and activating the device for use, at least one time, but the safety shield must be returned, automatically, to its locked, protective position immediately after use.

SUMMARY OF THE INVENTION

A surgical needle projects from the lower end of a tubular structure. A protective cover, or shield, in the form of a tubular sleeve, slightly larger than the tubular structure, has an upper end fitting over the lower end of the tubular structure. The lower end of the sleeve must completely cover and guard the sharp end of the needle. Elongated, generally axial, entrance and exit slots are formed in the tubular structure, between its lower and upper ends to engage a spring-loaded lug on the underside of the tubular sleeve. This allows the sleeve to move upward, with the lug sliding along the entrance slot of the tubular structure, to uncover the needle. The lug then rotates through a change-over slot, to the exit slot, to be forced downward and lock at the base of the exit slot, to recover and guard the needle. A spring connected between the tubular structure and the sleeve provides a radial torque to urge the lug from the entrance slot, through a change-over slot, toward the exit slot. The spring also provides an axial force to oppose the uncovering of the needle and to urge the sleeve, always, toward its needle-covering and locking position. The upper end of the tubular structure will be provided with a luer, or other fitting to couple the needle assembly to its intended function.

In accordance with the further embodiment of the invention, a tubular mount is provided with a hub attached to an upper end, an open lower end, and an aperture in a side of the mount. The hub has a needle extending from a lower end and a fitting at an upper end for coupling to a barrel and plunger assembly. A protective cover is provided having a diameter smaller than that of the mount so that an upper end of the cover fits inside of the lower end of the mount. The cover has an apertured lower end and is adapted for being in a needle protection position in which the tip of the needle is covered by the cover or a retracted position in which the needle extends through the apertured lower end of the cover to be exposed for use. A lug protrudes from a tab on the cover to engage the aperture in the side of the mount so that, as the cover is moved between the needle protection position and a retracted position, the lug moves in the aperture toward the upper end of the mount. The aperture includes an entrance position adjacent to the lower end of the mount and an armed position radially spaced from the entrance position by an angled portion of the mount. The needle protector is armed by rotating the cover to move the lug from the entrance position along the angled portion and to the armed position. A spring is coupled between the mount and the cover so that when the device is armed, a rotary torque is imparted to the spring. Movement of the cover to a retracted position upon actuation of the device causes the spring to be subjected to a compressive force. The torsional and compressive forces on the spring cause the lug to be urged back to the entrance position, thereby automatically causing the cover to return to the needle protection position.

In accordance with another embodiment of the invention, the needle protector device includes a needle subassembly having a hub from which the needle extends and ribs running axially along the exterior of the hub. The device further includes a tubular mount having an interior tapered channel through which the needle subassembly is guided during assembly. The ribs deflect slightly inward as the needle subassembly is urged through the channel and flare outward slightly once the subassembly has been pushed into the mount to retain the subassembly within the mount by an interference, or press fit attachment. The mount has an aperture for engaging a lug of a protective cover in assembly, as described above.

Protrusions are provided on the interior wall of the tapered channel of the mount to prevent rotation of the needle subassembly relative to the mount. More particularly, rotation of the needle subassembly is prevented by the interference of the protrusions with the ribs on the needle subassembly hub.

A spring coupled between the mount and the protective cover includes a pair of extensions, one extending axially from each end of the spring. In assembly, one of the spring extensions is inserted into an aperture in the mount and the other spring extension is inserted into an aperture in the cover. The cover and mount are then rotated by a multiple of 180° relative to one another in order to torsionally bias the spring. With the cover and mount thus rotated relative to one another, the cover and mount are coupled together by inserting the cover into the lower end of the mount. More particularly, an assembly ramp positioned axially with respect to the entrance position of the mount aperture receives the cover lug. The cover lug rides along the assembly ramp until the lug clears the ramp and enters the mount aperture through which the lug protrudes.

With this embodiment, a needle having an automatic protective mechanism and the ability to be re-armed further includes features facilitating simplified assembly. The press fit attachment of the ribbed needle hub to the tapered channel of the mount eliminates the need for sonic welding or solvent bonding. The axial spring extensions, the spring biasing achieved by rotating the cover and mount relative to one another, and the assembly ramp on the mount provide a simple scheme for biasing the spring in torsion and compression and for coupling the cover to the mount. Additional features include alignment grooves on both the cover and the mount for facilitating alignment between the cover and the mount for use in manual or automated assembly.

DETAILED DESCRIPTION OF THE INVENTION

Figure 1:
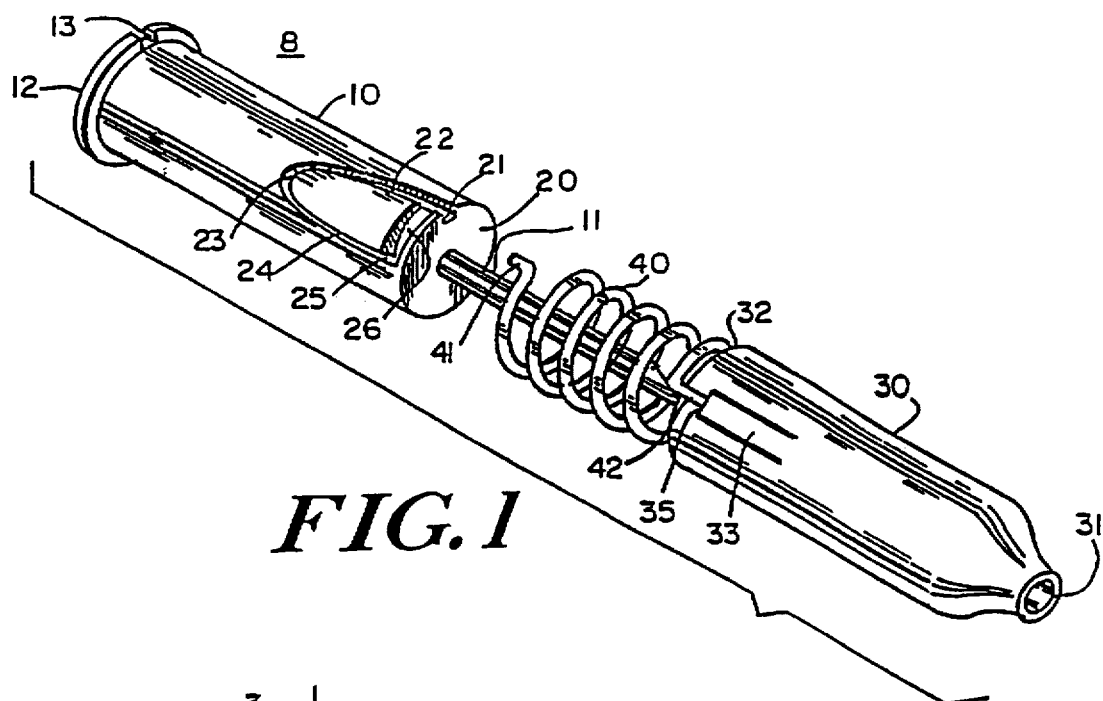
FIG. 1 shows an isometric, exploded view of the device.

Referring now more particularly to FIG. 1, and isometric view of the basic device 8 is shown in an exploded form to clearly illustrate the elements that interact to provide the automatic, safety, needle protector. An upper portion 10 is a hollow tubular mount that supports a needle 11 at one, lower end 20. The other, upper end has a flange 12, with a notch or slot 13 to accommodate the upper end 41 of a spring 40 in a manner that will be described later.

Figure 3:
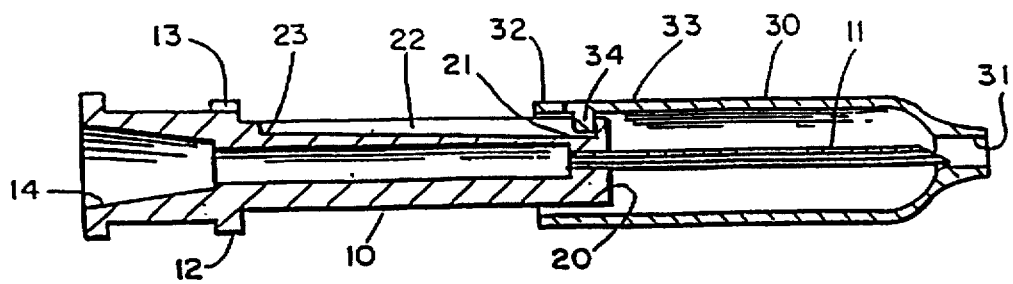
FIG. 3 shows a cross section of the device along the lines 3—3 of FIG. 2.

This other, upper end of the tubular sleeve 10 will, normally, include one of the conventional couplings for a syringe, such as the luer fitting 14 shown in FIG. 3. This has been omitted here, and in the other drawings, for simplicity. Other fittings for similar functions can also be accommodated.

The needle 11 is mounted in the center of the base 20 at the lower end of the tubular needle mount 10, in a well known manner. The sharp point, or tip, of the needle will be protected by a cover or sleeve 30.

This exploded view shows, quite clearly, typical slots in the needle mount that control the position and function of the protective cover 30 for the needle in a manner that will be illustrated in the other figures and described in more detail in due course.

These typical slots include an opening 21 for an elongated starting or entrance slot 22 that goes up to a change-over slot 23, that leads to an elongated exit slot 24 that ends in a locking ledge 25 that automatically locks the protective cover 30, with its lower end 31 over the needle.

The protective cover 30 has an opening 31 in its lower end that the needle can extend through when its inner lug 34 is moving through the slots 22, 23, and 24, and the device is in use. The other, upper end 32, as noted earlier, is open and forms the sleeve that fits loosely around the tubular needle mount 10. A notch 35 may be provided in the upper end 32 of the sleeve 30 to support the lower end 42 of the spring 40, as shown. This spring 40 provides the automatic operation of the protective cover.

Figure 4A:
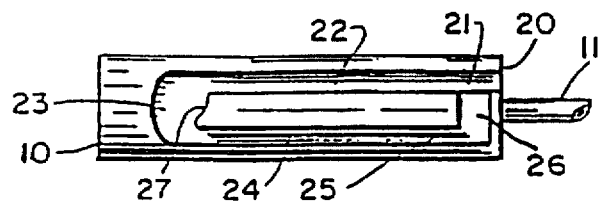
FIG. 4A shows a top view of the needle mount normal to the lines 4—4 of FIG. 2.
Figure 4:
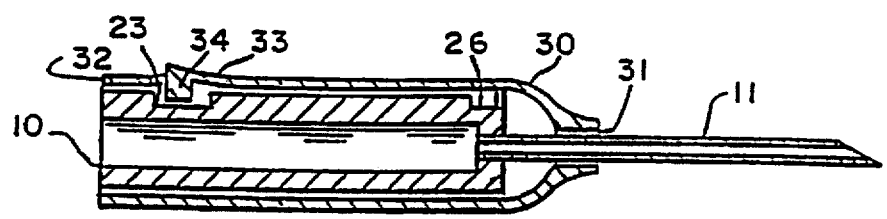
FIG. 4 shows a cross section of the device along the lines 4—4 of FIG. 2.
Figure 5:
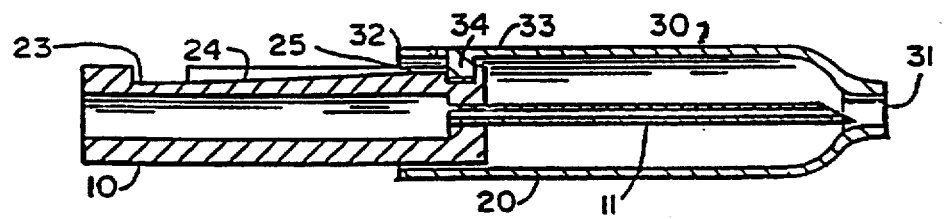
FIG. 5 shows a cross section of the device along the lines 5—5 of FIG. 2.

Another, flat spring 33 actuates a lug or cam 34, seen in FIGS. 3, 4, and 5, that rides in the slots 21 through 26 for the automatic control of the protective sleeve.

The spring 40 would, in operation, fit loosely over the tubular needle mount 10. The upper end clip 41 would fit into, and may be secured in the notch or slot 13 of the flange 12. The lower end clip 42 would fit into the notch or slot 35, as noted earlier, and may also be secured therein.

Figure 2:
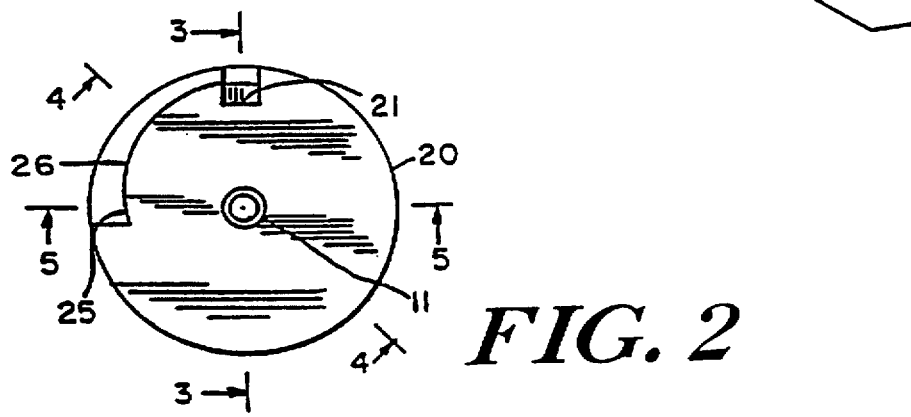
FIG. 2 shows a plan view of the needle mount.

FIG. 2 shows a plan view of the lower end 20 of the tubular needle mount, seen along the needle 11. This, more clearly, shows the opening 21 for the start of the lug 34, mounted on the underside of the spring 33, through its automatic locking path. This also shows the ledge 25, at the end of the slot 24, that secures the lug or cog 34 and locks the protective cover 30, with its end 31 well over the sharp end of the needle. Actually, the needle can be reactivated by rotating the sleeve 30, and moving its cog up the ramp 26 to drop back into the starting slot at 21.

FIG. 3 shows a cross section of the device along the lines 3—3 of FIG. 2. This shows the protective sleeve 30 with its upper end 32 over the tubular mount 10, its lower end 31 covering and protecting the sharp end of the needle 11, and its cog 34 started in the opening 21. The slot 22 will guide the cog to the change-over slot 23, and may raise it partially in the process. This figure also shows the flange 12, with the notch or slot 13 to accommodate the upper, outer end clip 41 of the spring 40.

The spring 40 is not shown in this and the subsequent drawings for simplicity and clarity in illustrating the other, most important elements of the safety cover, and their complex functions.

A typical luer fitting 14 is illustrated in this figure. Obviously this—or a similar coupling—would be necessary for coupling this safety device to any conventional unit that needs a hypodermic needle, which is the normal function of this device.

FIG. 4 shows another cross section of this device along the lines 4—4 of FIG. 2. This shows the protective sleeve or cover 30 drawn to the upper end of the tubular mount 10. This shows the cog 34, on the flat spring 33 of the sleeve 30 in the cross-over slot 23, and the needle fully exposed. As in all of these figures, similar elements are similarly numbered. The luer fitting 14 is, again, omitted for simplicity in this and the rest of these drawings.

FIG. 4A is a top view of the tubular mount 10 for mounting the needle 11, normal to the lines 4—4 of FIG. 2, and is added to illustrate another variation of the slots 21 through 26. This is the version that is, actually, used in the drawings 3, 4, and 5. To this has been added a notch 27 along the cross-over 23. This would hold the lug 34 against the pressures of the spring and would allow the protective cover 30 to be held with the needle exposed, if necessary, while it is being inserted or used. Subsequent movement or use of the cover 30 would complete the cycle, along the path of the lug 34, to the slot 24 and to the ledge 25, to lock the protective cover 30 in its safe position.

This figure also shows more depth to the cross-over 23. Actually this cross-over could extend from near the top of the slots to near the lower end of the mount. This could provide the essential, automatic safety locking of the sleeve with a minimal penetration of the needle, which might be advisable in many cases.

FIG. 5 is another cross section of the device, along the lines 5—5 of FIG. 2, and this shows the protective cover at the end of its cycle, with the lug 34 of the protective cover system locked against the ledge 25, and the end of the cover 31 well over the tip of the needle 11.

Figure 6:
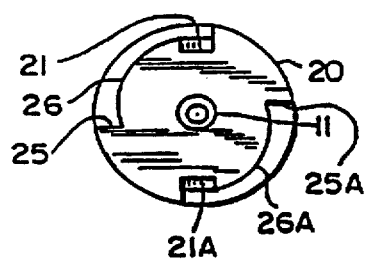
FIG. 6 shows a plan view of another variation of the needle mount.

This shows the cross-over slot 23 and the slot 24 with its ramp that carries the cog 34 up until it passes over the ledge 25, where the pressure of the spring 33 depresses the lug 34 to lock the safety shield in its safe condition. The spring 40, of course, in its axial pressure urges the cover and lug along the slot 24 to the locking position. FIG. 6 is another plan view of the bottom 20 with a variation of the needle holder, again in line with the needle 11. This shows an additional slot 21A, a ledge 25A, and a resetting slope 26A to accommodate an additional lug, not shown, to double the strength and the safety of the automatic locking function. Additional combinations of slots and lugs could, obviously, be added for additional strength and safety.

In operation, the device would normally be assembled with the elements of FIG. 1 compressed to the profile of FIG. 3. For example, the spring 40 would fit loosely over the tubular needle mount 10, with its upper end 41 seated in the notch 13 of the mount. This holds the protective cover, or sleeve 30 with its outer end 31 covering the sharp end of the needle 11, and its inner end fitting over the lower end 20 of the tubular needle mount. The lower end of the spring 42 is secured into the slot 35 of the protective cover, to hold the cog 34, mounted in the cover, in line with and against the ledge 25 so that the protective cover cannot be pushed back to expose the sharp end of the needle, whether it has been used or not.

When it is time to use the needle, for any reason, the needle mount 10 can be coupled to an appropriate syringe, or other device at its fitting 14. The cover or sleeve 30 can then be rotated—in this case clockwise—to move the cam 34 up the slope 26 to drop into the opening 21 at the start of the slot 22. This puts a rotary torque on the spring 40 which urges the cam back to the angle of the slot 24, which leads back to its locking ledge 25. However, the only way the cam can get back from its starting position 21 is to slide along the slots 22, 23, and 24 to be lifted and dropped back into the locking position at 25.

In other words, once the protective cover or sleeve is armed or cocked, the spring exerts a rotary pressure on the cover to urge the cam back towards its exit slot 24, and its locking position at 25. The spring also exerts an axial pressure on the cover to hold it in position over the sharp end of the needle until it is being used. The spring is then compressed axially to expose the needle for use, while moving the cam along the slots 22 and 23. Then the cam can only follow the slot 24 to return the cam, automatically, by the combined rotary and axial pressures of the spring, to its safe, locking position over the ledge 25, where the sharp end of the now used needle is automatically and permanently protected against accidental penetration of anything or anybody.

The spring, here, has this double function, and insures the automatic operation of the safety protective cover. The spring may be made of any springy material, from metal to plastic, and may be of any suitable, functional shape. Actually, the spring 40 may be molded as part of the sleeve 30, when suitable materials are chosen.

The materials chosen would presumably be of plastic. Both the protective cover, with or without the spring, and the tubular mount for the needle would, obviously, be molded for mass production and cost effectiveness. While the safety of medical workers is of prime importance, the cost of providing safety should be reasonable. The object of this invention is to provide the best possible, and almost foolproof protection, at a minimal cost.

It should be noted that these units are disposable—as must all needle mounts be—but these are permanently protected wherever they are disposed. The law, of course, meticulously requires a very special disposal of all medical wastes, which means there is no problem. However, sadly, human error, indifference, or duplicity loads our beaches and other facilities with medical wastes.

The mount 10 that physically supports the needle, which is the essential element of this device, is standard, and similar to many standard needle holders, that couple a needle to a luer, or other fitting, for its ultimate use. However, this unit may be slightly longer to accommodate the motion of the protective sleeve over the needle and mount.

The length of the sleeve, and the mount, will vary with the length and size of the needle, which will vary according to its many uses. The size and shape of the device will vary, along with the ultimate use. This will, again, be a function of the size, and length of the needle. The smallest possible would, of course, be most desirable.

A solid, thin cap over the base 20, at the lower end of the mount would be very easy to attach, and desirable for locking the lug in both directions. This would prevent the sleeve from being pulled off the needle mount, as well as from being pushed in to expose the needle, which would virtually eliminate exposure of the needle in any manner. In this case, a secondary means for raising the spring 33 would be needed to fit the lug 34 in either the starting slot or the locking ledge.

This could also avoid the need for, or use of the slope 26, which could be eliminated, to avoid the accidental rotation of the sleeve to arm the device.

The protective sleeve 30, as well as most of the rest of the device, would be of plastic for ease of manufacture. The sleeve should be as small as practical, and quite transparent to allow the needle to be seen and controlled. The opening at 31 may be the full size of the sleeve, or may be just large enough, as shown, for the needle to fit through.

Figure 7:
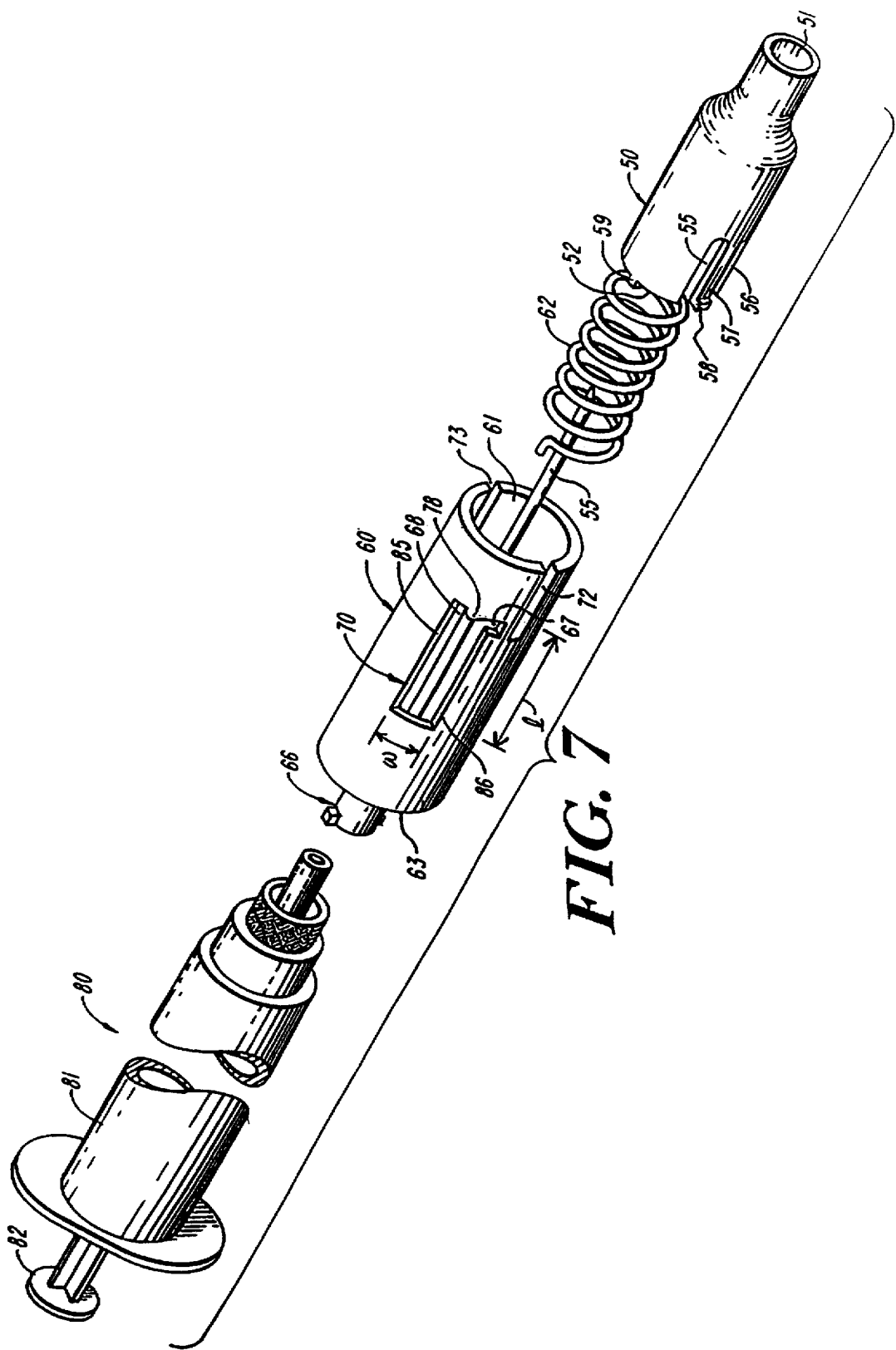
FIG. 7 shows an isometric, exploded view of a further embodiment of the invention with an exemplary barrel and plunger assembly.
Figure 8:
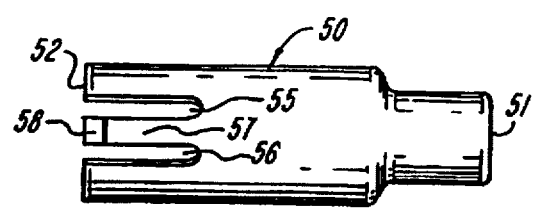
FIG. 8 shows a side view of the protective cover of the device of FIG. 7.

Referring to FIG. 7, a further embodiment of the invention is shown to include a protective cover, or sleeve 50 which fits inside a hollow, tubular mount 60. The protective cover 50 has an opening 51 at its lower end of a diameter suitable for permitting a needle 55 to extend therethrough during use. The diameter of the upper end 52 of the cover 50 is smaller than that of the mount 60 into which the cover extends. The protective cover 50 includes a pair of notches 55, 56 at the upper end 52 which are spaced to provide a cantilevered tab 57 therebetween. An upper end of the tab 57 has a lug 58 protruding therefrom, as shown also in FIG. 8. The cantilevered arrangement of tab 57 provides the tab with a resiliency which is advantageous during assembly of the device, as will be described.

Figure 9:
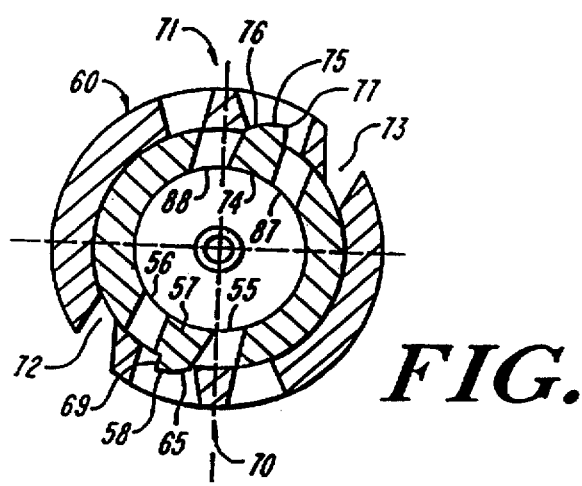
FIG. 9 shows a cross sectional view of the assembled device of FIG. 7.

Referring also to FIG. 9, a second, like tab 74 and a second pair of notches 87, 88 are provided in the upper end of the cover 50 at opposing locations with respect to the tab 57 and notches 55, 56, respectively. The second tab 74 has a lug 75 protruding therefrom, like lug 58. Each of the lugs 58, 75 has a tapered edge 65, 76, respectively, which further facilitate assembly of the device, and a flat edge 69, 77, as shown.

A spring 62 provides automatic operation of the protective cover 50 in response to axial and torsional forces applied during operation, as will be described. Suffice it here to say that the spring 62 is coupled between the protective cover 50 and the mount 60 with a lower end of the spring 62 attached to the cover 50 and an upper end attached to the mount 60. Specifically, the lower end of the spring has a hook portion which extends through a loop 59 on the upper end 52 of the cover 50.

The hollow, tubular mount 60 has an open lower end 61 for receiving the upper end 52 of the protective cover 50 and an upper end 63 coupled to a hub 66. More particularly, the upper end 63 of the mount 60 has an opening for receiving the hub 66, as can be seen in the cross-sectional views of FIGS. 11 and 12. The hub 66 supports the needle 55 at a lower end and has a coupling, or fitting, such as a luer fitting, at an upper end for mating with a conventional syringe barrel and plunger assembly. One exemplary assembly 80 is shown in FIG. 7 to include a barrel 81 and plunger 82. Various means for fastening the hub 66 to the mount 60 are suitable, such as sonic welding. Both the barrel and plunger assembly 80, as well as the hub and needle assembly 66 may be conventional, commercially available assemblies. The spring 62 is secured to the upper end of the mount 60 by locating the upper end of the spring 62 in a hole 64 in the upper end 63 of the mount 60 (see FIGS. 11 and 12).

Referring also to FIG. 9, the tubular mount 60 has two apertures 70, 71 and a pair of slots 72, 73, each one corresponding to one of the apertures 70, 71, respectively, and being spaced therefrom. Slots 72, 73 facilitate assembly of the device, as will be described. Each of apertures 70, 71 has a width labelled "w", a length labelled "l", and permits the protective cover 50 to be in a needle protection position, an armed position, or in one of a plurality of retracted positions during use of the device when the needle 55 is exposed.

Considering exemplary aperture 70 and slot 72, the lug 58 engages the aperture 70 and is moveable within the constraints of the aperture 70 to provide the cover 50 in the needle protection position, the armed position, or a retracted position. That is, the lug 58 protrudes through the aperture 70, slightly beyond the inner diameter of the mount 60, so that the edges, or walls of the aperture 70 restrict the movement of the lug 58 and cover 50. However, preferably, the lug 58 does not protrude beyond the outer diameter of the mount 60 in order to prevent potential undesirable interference with actuation of the device.

The needle protection position of the cover 50 corresponds to the lug 58 being located in a first, entrance position 67 of the aperture 70. The armed position corresponds to the lug 58 being in a second, armed position 68 of the aperture 70. When the cover 50 is in a retracted position, the lug 58 is located above the entrance and armed positions 67, 68 and toward the upper end of the mount 60 between an entrance wall 85 and an exit wall 86 of the aperture 70. The entrance and armed positions 67, 68 of the mount aperture 70 are radially spaced by an angled portion 78 of the mount 60. While the operation of the device is described with respect to exemplary lug 58 and aperture 70, it is understood that aperture 71 has like features for engaging corresponding lug 74.

The mount 60 and the protective cover 50 may be comprised of any material having suitable strength and other desired characteristics, such as plastic. Additionally, the mount 60 and cover 50 may be manufactured by any conventional technique, such as injection molding. Preferably, the cover 50, and at least the lower end 51 thereof, is made from a transparent material so that the tip of the needle 55 is visible in order to facilitate proper insertion into a needle receiving surface, such as a patient's arm. Spring 62 may be made of any suitable material providing a spring characteristic, such as metal or plastic. It should be understood that the selected materials and method of manufacturing the components of the device will vary in accordance with, inter alia, application requirements and cost considerations.

In assembling the device, mount 60 is fastened to the hub 66 as noted above, such as by a sonic welding process. The upper end of the spring 62 is positioned in the hole 64 at the upper end 63 of the mount 60 and the lower end of the spring 62 is attached to the cover 50 and specifically, to the loop 59. With the spring 62 thus coupled between the mount 60 and the cover 50, the cover 50 is guided into the larger diameter mount 60 with tabs 57, 74 aligned with corresponding slots 72, 73. Once the cover 50 cannot be inserted further into the mount 60 (i.e., once lugs 58, 75 contact the upper ends of the slots 72, 73), the cover 50 is rotated clockwise. Upon such rotation of the cover 50, the cantilevered tabs 57, 74 are deflected slightly inward toward the inside of the mount 60. This rotation of the cover 50 is facilitated by the tapered edges 65, 76 of the lugs 58, 75, respectively.

Figure 10:
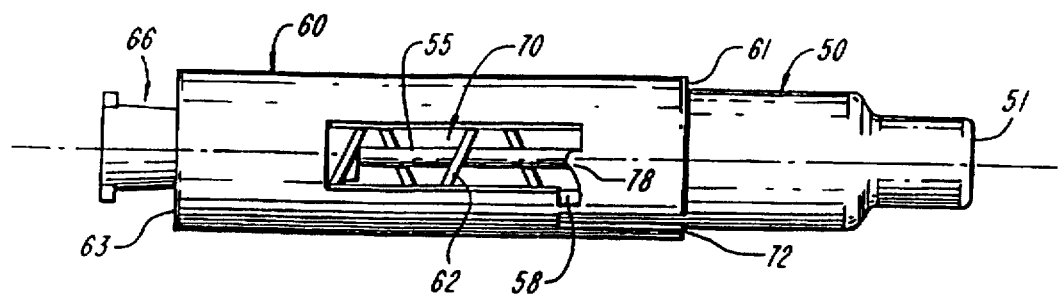
FIG. 10 shows a side view of the assembled device of FIG. 7.

Considering exemplary slot 72, aperture 70, and lug 58, once the lug 58 enters the entrance position 67 of aperture 70, the cover 50 is prevented from rotating counterclockwise due to the flat edge 69 of the lug 58 contacting the side of the entrance position 67 of the mount 60 adjacent to the slot 72. The assembled device is shown in FIG. 10 with the lug 58 positioned in the entrance position 67 of the aperture 70. In this position, the protective cover 50 extends over the tip of the needle 55 and cannot be pushed straight back to expose the needle 55 since the back wall of the entrance position 67 prevents such movement of the lug 58. With the cover 50 disposed in this needle protection position, the spring 62 is in a partially compressed state. Additionally, the spring 62 is subjected to a slight rotary torque, or torsional force, as a result of the rotation of the spring 62 as the cover 50 was rotated to move the lug 58 from the slot 72 to the entrance position 67.

When use of the needle 55 is desired, the hub 66 is coupled to a conventional syringe barrel and plunger assembly, such as the exemplary assembly 80 shown in FIG. 7. The upper end of the hub 66 has a fitting, such as a luer fitting, for this purpose. Thereafter, the device may be armed, or cocked, in preparation for use by rotating the cover 50 clockwise which causes the lug 58 to move along the angled portion 78 of the mount 60 that separates the entrance position 67 from the armed position 68. As the lug 58 clears the angled portion 78, an audible click occurs, indicating to the user that the device is armed and ready for use. By moving the lug 58 to the armed position, an additional rotary torque is exerted on the spring 62 which, upon actuation of the device, urges the lug 58 back to the entrance position 67.

Figure 11:
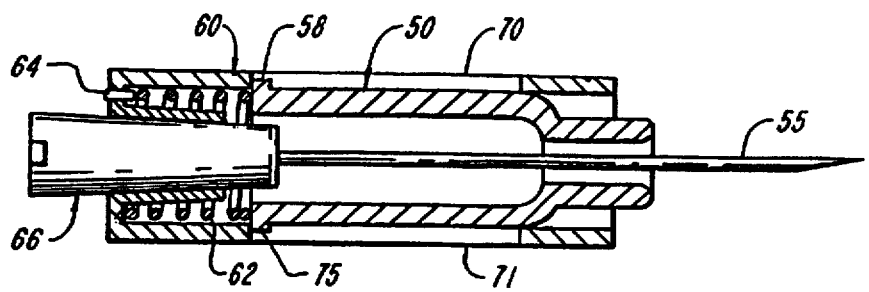
FIG. 11 shows a cross sectional view of the assembled device of FIG. 7 with the protective cover in a retracted position.
Figure 12:
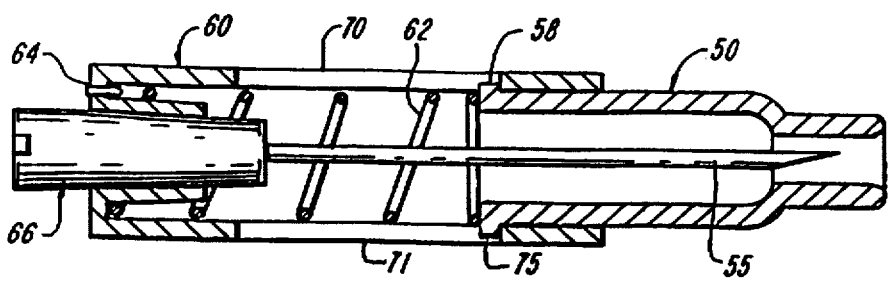
FIG. 12 is a cross sectional view of the assembled device of FIG. 7 with the protective cover in a needle protection position.

As the lower end of the cover 50 is pushed against a needle receiving surface, the cover 50 is forced further inside the mount 60, as shown in the view of FIG. 11. Such actuation of the device causes the spring 62 to be subjected to an additional axial, compressive force, as is apparent from the view of FIG. 11, and causes the lug 58 to move from the armed position 68 along the entrance wall 85 of the slot 70 and toward the upper end of 63 of the mount 60.

The torsional and compressive forces exerted on the spring 62 urge the protective cover 50 back to the needle protection position in which the lug 58 is located in the entrance position 67. Thus, upon removal of the needle 55 from the receiving surface, the protective cover 50 automatically moves to the needle protection position in which the needle tip is covered. Specifically, the rotary torque on the spring 62 causes the cover 50 to move radially, rotating counterclockwise so that the lug 58 contacts the exit wall 86 and the compressive force on the spring 62 causes the cover 50 to move outward from the mount 60 to the needle protection position shown in FIGS. 10 and 12. It is noted that once the lug 58 has returned to the entrance position 67, the device may be reactivated by re-arming the device for further use. That is, once the lug 58 has returned to the entrance position 67, the device can be re-armed by rotating the cover 50 clockwise which causes the lug 58 to move along the angled portion 78 of the mount 60 separating the entrance position 67 and the armed position 68, in the manner described above.

In view of the above described operation of the device, it should be understood that the dimensions of the apertures 70, 71 may be varied in accordance with a particular application. For example, a longer needle 55 may require that the aperture 70 have a greater length "l" to permit a desired exposure of the needle 55. Additionally other device dimensions, such as those of the mount 60 and the cover 50, may be readily varied as required in a particular application.

While the embodiment of FIGS. 7–12 is shown to have two opposingly disposed tabs 57, 74, apertures 70, 71, and slots 72, 73, it should be appreciated that a single tab, aperture, and slot arrangement may be suitable in certain applications.

The needle protector arrangements described herein are useable with conventional syringe barrel/plunger assemblies, such as the exemplary assembly 80 of FIG. 7, so that inventory of such assemblies need not be discarded and replaced in order to use the described devices. Additionally, by modifying the mount 10 to provide slots 22–26 (FIGS. 1–6) and the mount 60 to provide apertures 70, 71 (FIGS. 7–12), the advantages of the present needle protector embodiments are achieved without requiring additional parts.

Figure 13:
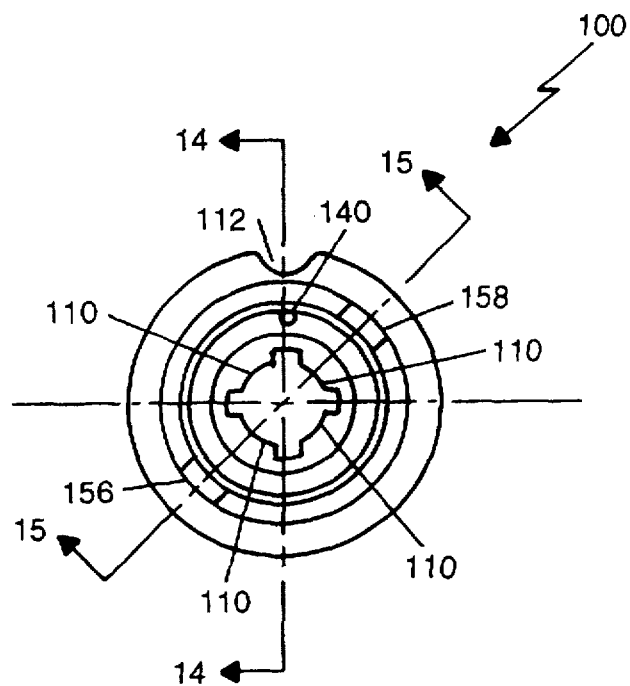
FIG. 13 is an end view of an alternate embodiment of the needle protector mount.
Figure 14:
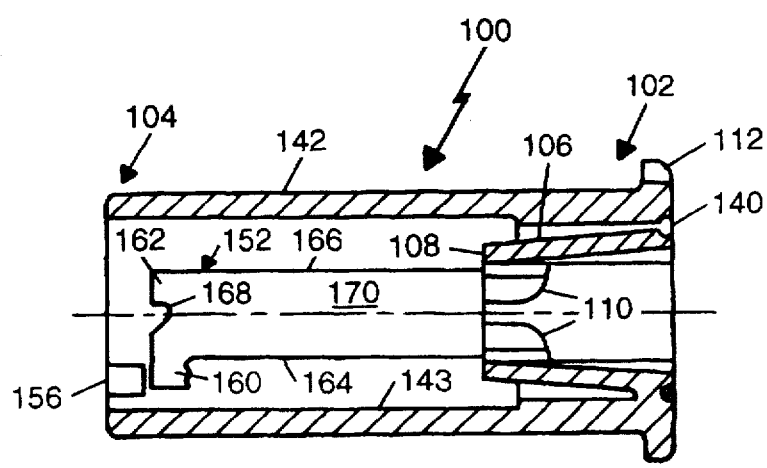
FIG. 14 is a cross sectional view of the mount of FIG. 13 taken along line 14—14 of FIG. 13.
Figure 15:
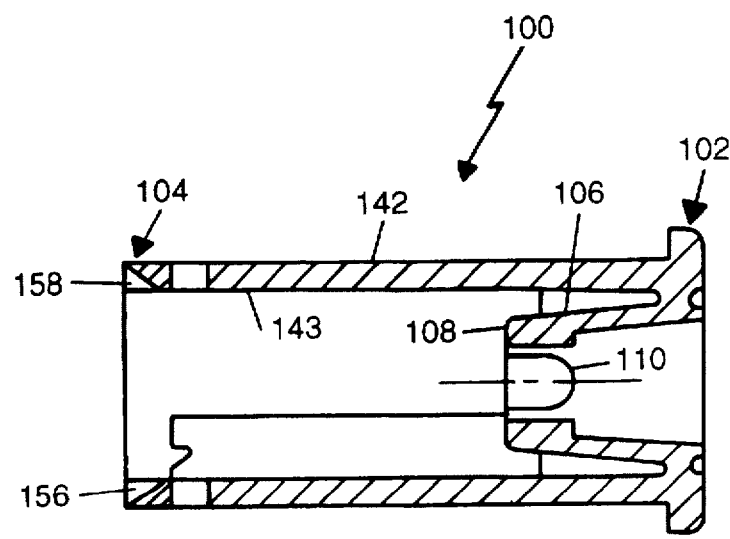
FIG. 15 is a cross sectional view of the mount of FIG. 13 taken along line 15—15 of FIG. 13.

Referring to FIGS. 13–15, various views of an alternate needle protector mount 100 are shown. FIG. 13 is an end view of the mount 100. FIG. 14 is a cross-sectional side view of the mount 100 taken along line 14—14 of FIG. 13 and FIG. 15 is an alternate cross-sectional side view of the mount 100 taken along line 15—15 of FIG. 13.

The mount 100 is substantially cylindrical, or tubular in shape and has an upper end 102 and an open lower end 104. An interior channel 106 extends from the upper end 102 of the mount to terminate at a terminal end, or edge 108. The channel 106 is tapered such that the diameter of the channel 106 at the terminal edge 108 is reduced relative to the diameter of the channel 106 adjacent the upper end 102 of the mount 100. During assembly, a needle subassembly, such as that shown in FIG. 16, is coupled to the mount 100 by insertion into the tapered channel 106.

Figure 16:
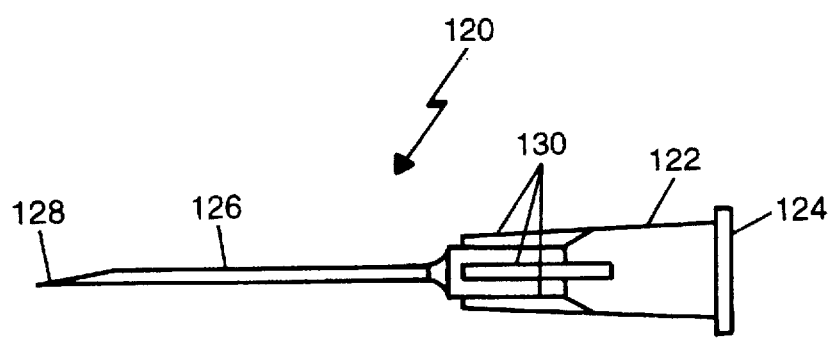
FIG. 16 is a side view of a needle subassembly.

Referring also to FIG. 16, a needle subassembly 120 includes a hub 122 having a luer fitting 124 at a first end and a needle 126 extending from a second end to terminate at a tip 128, as shown. The luer fitting 124 is adapted for connection to a conventional syringe barrel and plunger assembly. The hub 122 has a plurality of ribs 130 extending axially with respect to the needle 126 along the exterior surface of the hub 122.

The hub 122 is comprised of a plastic material having some resiliency. The smallest inner diameter of the mount channel 106, adjacent the terminal edge 108, is slightly smaller than the outer diameter of the hub with the ribs 130. With this arrangement, a press fit attachment of the needle subassembly 120 to the mount is achieved, as described below.

The needle subassembly 120 may be a conventional, commercially available assembly, as is available from Becton Dickinson & Co. of Rutherford, N.J. In one embodiment, the needle 126 is one inch long. Use of a one inch needle is advantageous, as compared to use of a longer needle, since the shorter needle is less susceptible to bending and thus, is stronger.

The mount 100 has a plurality of stops 110 protruding from the interior walls of the channel 106 into the diameter of the channel 106. Two such stops 110 are visible in the view of FIG. 14 and one stop 110 is visible in the view of FIG. 15. In assembly, the hub ribs 130 are aligned with the mount 100 such that the ribs are disposed between the stops 110. With this arrangement, the stops 110 prevent the needle subassembly 120 from rotating relative to the mount 100 once the subassembly 120 is press fit into the mount 100.

A spring receiving aperture 140 (FIGS. 13 and 14) is disposed in the upper end 102 of the mount 100 between the mount exterior wall 142 and the channel 106, as shown. In assembly, the spring receiving aperture 140 receives one end of a spring, such as the spring 144 shown in FIG. 21 and discussed below.

The mount 100 includes two apertures 152, 154 (only one of which can be seen in the views of FIGS. 14 and 15) and a pair of assembly ramps 156, 158 (FIGS. 13 and 15), each one corresponding to one of the apertures 152, 154. Each of apertures 152, 154 is substantially identical to like apertures 70, 71 described above in conjunction with the embodiment of FIGS. 7–12. As labelled on illustrative aperture 152, each aperture has an entrance position 160, an armed position 162 radially spaced from the entrance position by an angled protrusion 168, and an elongated portion 170 extending toward the upper end 102 of the mount between an entrance wall 164 and an exit wall 166 of the aperture.

Assembly ramps 156, 158 are tapered, or angled portions of the inner wall 143 of the mount 100 extending from the lower end 104 of the mount 100 toward the respective aperture 152, 154, as shown in FIG. 15. The taper of the ramps 156, 158 is such that the wall is thinnest at the portion of the ramp adjacent to the lower end 104 of the mount 100 and is thickest at the portion of the ramp adjacent to the respective aperture 152, 154. The assembly ramps 156, 158 facilitate attachment of the protective cover, such as cover 180 of FIGS. 17–20, to the mount 100 by gradually increasing the deflection of the cover lugs until the lugs enter the respective aperture 152, 154, as described below.

The mount 100 includes an alignment groove 112 shown in FIGS. 13 and 14 extending axially along wall 142. Groove 112 facilitates alignment of the mount 100 during manual or automated assembly of a needle protector including the mount 100 by providing a reference relative to which the mount 100 can be aligned.

Figure 19:
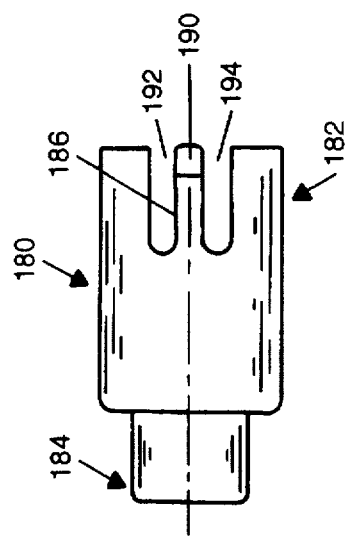
FIG. 19 is a side view of the protective cover of FIG. 17.
Figure 20:
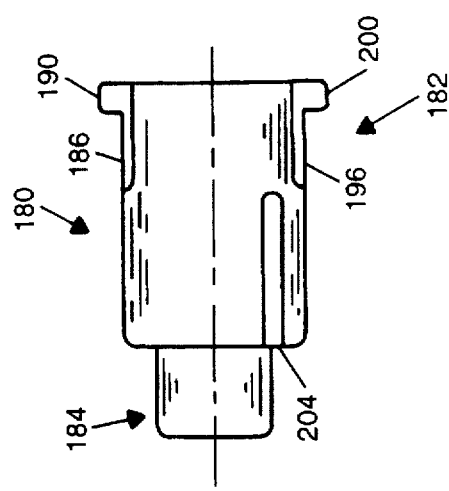
FIG. 20 is an alternate side view of the protective cover of FIG. 17.
Figure 18:
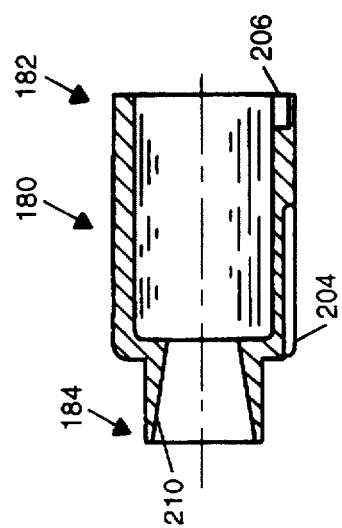
FIG. 18 is a cross sectional view of the protective cover of FIG. 17 taken along line 18—18 of FIG. 17.
Figure 17:
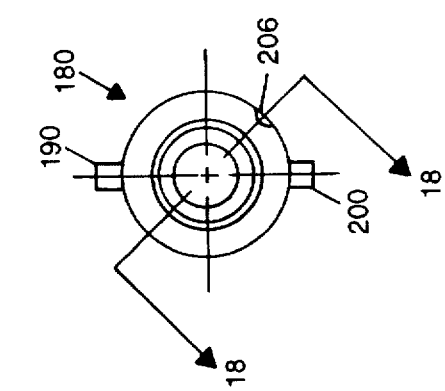
FIG. 17 is an end view of an alternate embodiment of the protective cover.

Referring now to FIGS. 17–20, an alternate protective cover 180 is shown. FIG. 17 is an end view of the cover 180, FIG. 18 is a cross-sectional view of the cover taken along line 18—18 of FIG. 17 and FIGS. 19 and 20 are alternate side views of the cover 180 showing its various features.

The protective cover 180 is substantially cylindrical and has an upper end 182 of an outer diameter slightly smaller than the inner diameter of the lower end 104 of the mount 100, permitting the upper end 182 of the cover 180 to be received within the lower end 104 of the mount 100. A lower end 184 of the protective cover 180 has a reduced diameter relative to the diameter of the upper end 182, so as to prevent a finger from being inserted through the open lower end 184 to contact the needle 126.

The protective cover 180 includes a first pair of notches 192, 194 (FIG. 19) at the upper end 182 which are spaced to provide a cantilevered tab 186 therebetween. An upper end of the tab 186 has a lug 190 protruding therefrom. The cantilevered arrangement of tab 186 provides the tab with a resiliency which is advantageous during assembly of the device, as will be described. The protective cover 180 includes a second pair of notches (not shown) identical to notches 192, 194 which provide a second tab 196 cantilevered therebetween with a lug 200 protruding therefrom. The second tab 196 is positioned 180° from the first tab 186. The first and second lugs 190, 200 are adapted for engaging the first and second apertures 152, 154 of the mount 100 in assembly, respectively. As noted above with respect to the embodiment of FIGS. 7–12, in some applications, a single cover lug and mount aperture arrangement may be suitable.

The mount 100 and the protective cover 180 may be comprised of any material having suitable strength and other desired characteristics, such as plastic. Additionally, the mount 100 and cover 180 may be manufactured by any conventional technique, such as injection molding. Preferably however, the cover 180 is made from a transparent material so that the tip of the needle 126 is visible in order to facilitate insertion into a needle receiving surface, such as a patient's arm.

It is further preferable that the mount 100 and cover 180 be comprised of different materials in order to reduce any sticking therebetween over time. In one embodiment, the mount 100 is comprised of the copolymer styrene-acrylonitrile (SAN) from Monsanto of St. Louis, Mo. and the protective cover 180 is comprised of a polycarbonate from GE Plastics of Pittsfield, Mass.

Additional features of the protective cover 180 include an alignment groove 204 in the exterior surface of the mount 100, as shown in FIGS. 18 and 20. The alignment groove 204 facilitates assembly of the device by providing a reference feature with which the cover 180 can be aligned, or oriented during assembly. The alignment groove 204 permits ready alignment of the cover 180, whether assembly is manual or automated, and can be used in conjunction with the mount alignment groove 112 (FIGS. 13 and 14) to facilitate alignment of the mount 100 relative to the protective cover 180 as the lugs 190, 200 of the cover 180 are directed along the respective assembly ramps 156, 158 of the mount.

A spring receiving aperture 206 is disposed in a wall of the protective cover 180, as shown in FIGS. 17 and 18. Specifically, the spring receiving aperture 206 is positioned at the upper end 182 of the protective cover 180 for receiving an end of a spring, such as spring 144 shown in FIG. 21.

An additional feature of the protective cover 180 is provided by the tapered inner wall portion 210 adjacent to the reduced diameter lower end 184 of the cover 180. The wall portion 210 is tapered such that the wall is thickest at the portion distal from the lower end 184 and is thinnest at the portion adjacent to the end 184, as shown. The purpose of the tapered wall portion 210 is to prevent the needle 126 from gouging the wall of the cover 180 in instances where component tolerances are in a worst case condition. That is, in instances where the inner wall diameter of the mount 100 is at the high end of its specified tolerance range and the outer wall diameter of the protective cover 180 is at the low end of its specified tolerance range, the angled wall portion 210 prevents the needle tip 128 from gouging the cover wall.

Mount apertures 152, 154 permit the protective cover 180 to be in a needle protection position, an armed position, or in one of a plurality of retracted positions to expose the needle 126 during use of the device. The needle protection position of the cover 180 corresponds to the lugs of 190, 200 the cover 180 being located in the entrance position 160 of the respective aperture 152, 154. The armed position corresponds to the lugs 190, 200 being in the armed position 162 of the respective aperture 152, 154. When the cover 180 is in a retracted position, the lugs 190, 200 are located in the respective aperture portion 170, above the entrance and armed positions 160, 162 and toward the upper end 102 of the mount 100 between the entrance wall 164 and the exit wall 166 of the respective aperture 152, 154.

Figure 21:
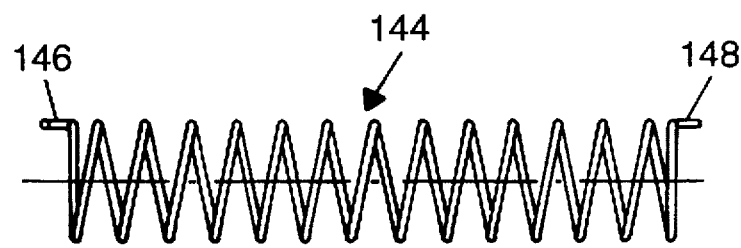
FIG. 21 is a side view of an alternate spring.

Referring to FIG. 21, an alternate spring 144 is shown to include a pair of extensions 146, 148, extending axially from opposite ends thereof. The extensions 146, 148 are adapted for engaging the spring receiving apertures 140, 206 of the mount 100 and the protective cover 180, respectively. Since the spring 144 has a symmetrical construction, issues regarding orientation of the spring during assembly are advantageously avoided. Spring 144 may be made of any suitable material providing a desired spring constant, such as metal or plastic.

Figure 22:
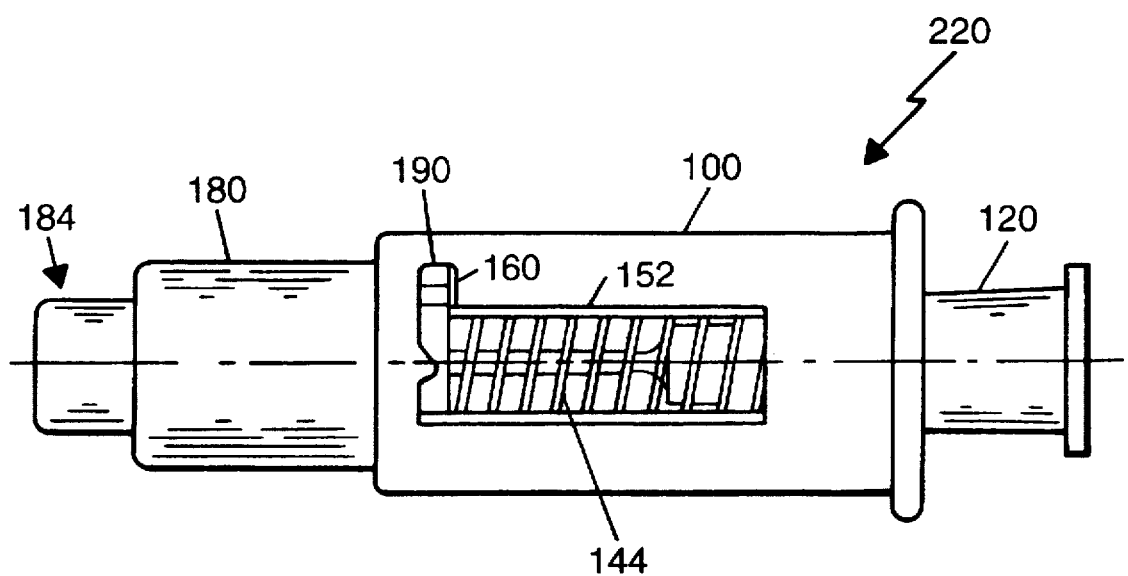
FIG. 22 is a side view of an alternate embodiment of the needle protector device including the mount of FIGS. 13–15, the needle subassembly of FIG. 16, the protective cover of FIGS. 17–20, and the spring of FIG. 21.
Figure 23:
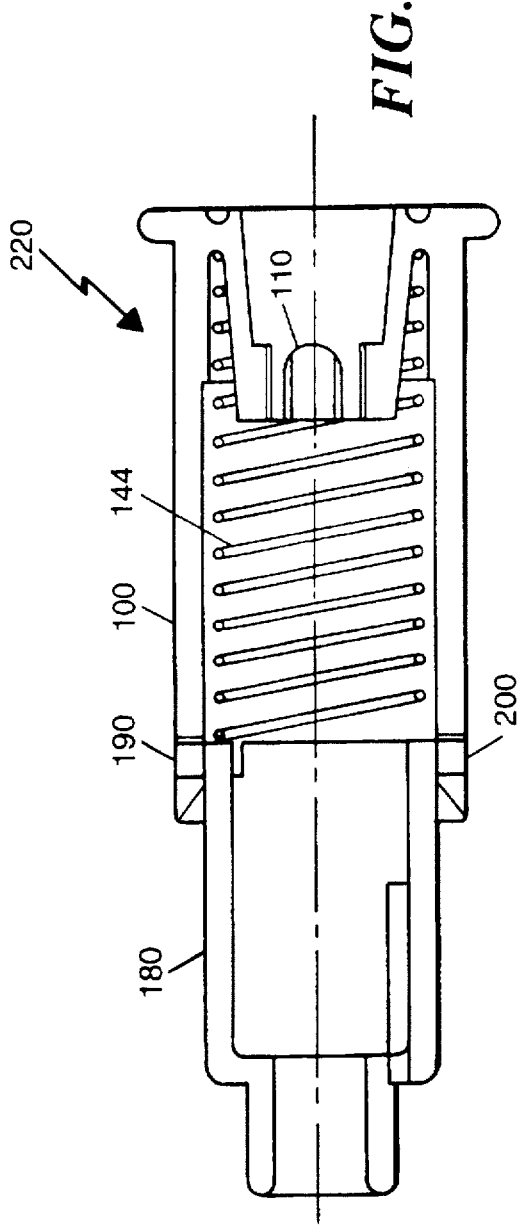
FIG. 23 is a cross sectional view of the needle protector device of FIG. 22 with the protective cover in the needle protection position.
Figure 24:
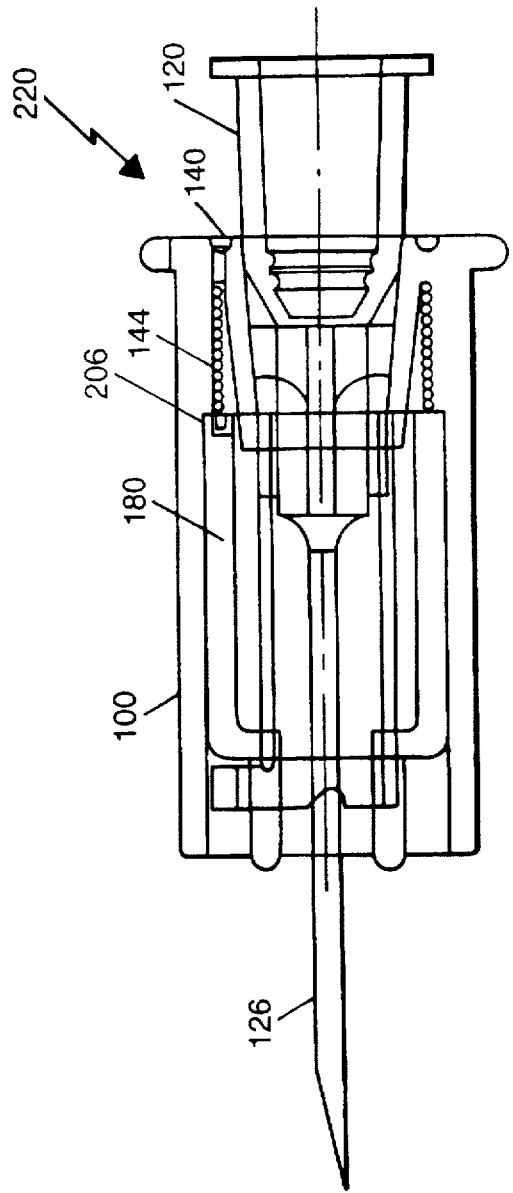
FIG. 24 is a cross sectional view of the needle protector device of FIG. 22 with the protective cover in a retracted position.

Referring now to FIGS. 22–24, an alternate needle protector device 220 is shown to include the mount 100 of FIGS. 13–15, the needle subassembly 120 of FIG. 16, the protective cover 180 of FIGS. 17–20 and the spring 144 of FIG. 21. Specifically, FIG. 22 is a side view of the device 220 with the cover 180 in the needle protection position. Thus, the lugs 190, 200 are in the entrance position 160 of the respective aperture 152, 154, as shown for lug 190 in aperture 152. A cross-sectional view of the needle protector device 220 without the needle subassembly 120 is shown in FIG. 23 and FIG. 24 is a cross-sectional view of the needle protector device 220 with the protective cover 180 in a retracted position, thereby exposing the needle 126 through the reduced diameter lower end 184 of the cover 180.

During assembly, the spring 144 is inserted into the lower end 104 of the mount 100 such that one of the spring extensions 146, 148 extends into the spring receiving aperture 140 at the upper end 102 of the mount, as shown in FIG. 24. With the spring 144 thus positioned, the other spring extension 146, 148 is aligned with the spring receiving aperture 206 of the protective cover 180.

Once the spring 144 is positioned with one extension inserted into the spring receiving aperture 140 of the mount 100 and the other extension inserted into the spring receiving aperture 206 of the cover 180, the mount 100 and the cover 180 are rotated by a multiple of 180° relative to one another to impart a torsional bias on the spring 144. Preferably, the mount 100 and cover 180 are rotated relative to one another by either 180° or 360°. This process can be readily performed with a simple fixture. Having thus biased the spring 144, the cover 180 is inserted into the mount 100.

Specifically, the cover lugs 190, 200 are aligned with a respective assembly ramp 156, 158, the upper end 182 of the cover 180 is inserted into the open lower end 104 of the mount 100. Alignment of the cover 180 and the mount 100 is facilitated by the alignment groove 204 on the cover 180 and the alignment groove 112 on the mount 100. As the cover 180 is urged inside the mount 100, the spring 144 is subjected to a compressional force. The lugs 190, 200 of the cover 180 are deflected inward as they ride along the respective ramp 156, 158, as is permitted by their cantilevered construction. The entrance position 160 of each aperture 152, 154 is located axially adjacent to the respective ramp 156, 158. Thus, as the cover 180 is urged into the mount 100, the lugs 190, 200 overcome the respective ramp 156, 158 and enter the entrance position 160 of the respective aperture 152, 154. Having entered the entrance position 160 of the respective aperture 152, 154, the lugs 190, 200 return to their initial non-deflected positions, thereby causing the lugs 190, 200 to be captured within the respective aperture 152, 154, as shown in the views of FIGS. 22 and 23. The cover 180 is prevented from separating from the mount 100, since the lugs 190, 200 are captured in respective aperture 152, 154. The spring 144 is biased both in torsion and compression once the mount 100 and cover 180 are coupled together in the above-described manner.

Having thus assembled the mount 100, cover 180, and spring 144, the needle subassembly 110 is inserted into the mount 100 from the upper end 102 thereof. As noted above, the ribs 130 of the needle subassembly 120 are aligned with the interior channel 106 of the mount 100 so as to be in axial alignment with regions of the interior channel 106 between the protrusions 110. With the needle subassembly 120 and the mount 100 thus aligned, the subassembly 120 is urged into the mount 100. Since the outer diameter of the hub 120, as defined by the ribs 130, is slightly larger than the inner diameter of the interior channel 106 adjacent to the terminal edge 108, pushing the needle subassembly 120 into the mount 100 provides an interference, or press fit interconnection between the subassembly 120 and the mount 100. This interference fit between the subassembly 120 and the mount 100 prevents the subassembly 120 from being pulled back out of the mount 100. As will be apparent to those of skill in the art, the needle protector device 220 is suitable for either manual or automated assembly.

The operation of the device 220 thus assembled is substantially identical to the operation of the needle protector embodiment of FIGS. 7–12. That is, when use of the device 220 is desired, the luer fitting 124 of the hub 122 is coupled to a conventional syringe barrel and plunger assembly, such as the illustrative assembly 80 shown in FIG. 7. The device 220 is then armed by rotating the cover 180 clockwise causing the lugs 190, 200 to ride along the angled portions 168 of the respective aperture 152, 154. As the lugs 190, 200 clear the respective angled portion 168, an audible click occurs, indicating to the user that the device 220 is armed and ready for use.

Actuation of the device 220 by pushing the cover 180 against a needle receiving surface forces the cover 180 further inside the mount 100, as shown in FIG. 24. In this retracted cover position, the lugs 190, 200 are positioned in portion 170 of the respective aperture 152, 154. The torsional and compressive forces exerted on the spring 144 during assembly cause the cover 180 to be automatically urged back over the needle tip and thus, cause the lugs 190, 200 to be automatically urged to return to the entrance position 160 of the respective aperture 152, 154. Once the lugs 190, 200 have returned to the entrance position 160, the device 220 can be re-activated or re-armed for further use.

The features of the needle protector 220 of FIGS. 22–24 permit a simple, effective, and relatively inexpensive manner of assembly. Specifically, the press fit attachment of the needle subassembly 120 to the mount 100 provides an effective way of securely attaching the subassembly 120 and mount 100, without requiring the hub 122 to be sonically welded or solvent bonded to the mount 100. The spring 144 simplifies manufacture of the device 220 by its symmetrical construction, thereby eliminating orientation issues. The axial spring extensions 146, 148 are further advantageous in their simplicity of engagement with the mount 100 and cover 180. Furthermore, this axial spring extension arrangement is conducive to biasing the spring 144 in torsion prior to attaching the cover 180 to the mount 100. The alignment grooves 112, 204 of the mount 100 and cover 180, respectively, as well as the assembly ramps 156, 158 of the mount 100 further enhance the ease with which the device 220 is assembled, as described above.

Having described the preferred embodiments of the invention, it will be apparent to one of skill in the art that other embodiments incorporating their concepts may be used. Accordingly, the invention should be limited only by the spirit and scope of the appended claims.

We claim:

1. A needle protector device comprising:
    a needle subassembly having a hub and a needle extending from said hub to terminate at a tip, said hub having at least one rib on an exterior surface;
    a mount having an upper end, an open lower end, and a tapered interior channel extending from said upper end of said mount, wherein said at least one rib of said hub is press fit into said channel in assembly to retain said needle subassembly in attachment to said mount; and
    a protective cover having an upper end coupled to said lower end of said mount and an open lower end, wherein said protective cover is adapted for being in a needle protection position in which said cover is disposed over said needle tip or in a retracted position in which said needle tip extends through said open lower is end of said cover.

2. The needle protector device recited in claim 1 wherein said mount has an aperture disposed in a side thereof, said aperture including an entrance position and an armed position radially spaced from said entrance position by a portion of said mount protruding into said aperture and wherein said cover has a lug for engaging said aperture of said mount so that, as said cover is moved between said needle protection position and said retracted position, said lug moves within said aperture, wherein said device is armed by rotating said cover to move said lug from said entrance position over said protruding portion of said mount to said armed position.

3. The needle protector device recited in claim 2 wherein said mount has an assembly ramp comprising a tapered inner wall portion of said mount extending from said lower end of said mount toward said aperture along which said lug rides during assembly.

4. The needle protector device recited in claim 1 wherein said cover has a diameter smaller than the diameter of said mount and wherein said upper end of said cover is disposed inside said lower end of said mount.

5. The needle protector device recited in claim 1 wherein said interior channel of said mount has at least one protrusion extending into said channel so that, in assembly, said at least one protrusion prevents said needle subassembly from rotating relative to said mount by interfering with said at least one rib.

6. The needle protector device recited in claim 1 wherein said lower end of said cover has a first wall thickness and said upper end of said cover has a second wall thickness greater than said first wall thickness.

7. The needle protector device recited in claim 1 further comprising a spring having a first extension extending axially from a first end of said spring and a second extension extending axially from a second end of said spring, said first extension being adapted for insertion into a spring receiving aperture in said mount and said second extension being adapted for insertion into a spring receiving aperture in said cover.

8. The needle protector device recited in claim 7 wherein said cover and said mount are rotated relative to one another prior to coupling said cover to said mount in order to rotationally bias said spring.

9. A device for protectively covering a needle comprising:
    a mount adapted for having said needle attached thereto at a first end and having an open second end through which said needle extends;
    a protective cover having a first end coupled to said open second end of said mount and an open second end; and
    a spring coupled between said mount and said cover, said spring being biased in compression and torsion when said cover is coupled to said mount, so as to automatically urge said cover to a needle protection position in which said cover is disposed over said needle.

10. The device recited in claim 9 wherein said spring has a first extension extending axially from a first end thereof and a second extension extending axially from a second end thereof, said first extension being adapted for insertion into a spring receiving aperture in said mount and said second extension being adapted for insertion into a spring receiving aperture in said cover.

11. The device recited in claim 10 wherein said mount and said cover are rotated relative to one another by at least 180° prior to coupling said cover to said mount during assembly in order to rotationally bias said spring.

12. The device recited in claim 9 wherein said mount has an aperture disposed in a side thereof, said aperture including an entrance position and an armed position radially spaced from said entrance position by a portion of said mount protruding into said aperture and wherein said cover has a lug for engaging said aperture of said mount so that, as said cover is moved between said needle protection position and said retracted position, said lug moves within said aperture, wherein said device is armed by rotating said cover to move said lug from said entrance position over said protruding portion of said mount to said armed position.

13. The device recited in claim 9 wherein said cover has a diameter smaller than said mount and wherein said first end of said cover is disposed inside said second end of said mount.

14. The device recited in claim 9 wherein said needle is attached to a hub having at least one rib and said mount has an interior channel extending from said first end of said mount for receiving said hub, said interior channel having at least one protrusion extending into said channel and wherein, in assembly, said at least one protrusion prevents said hub from rotating relative to said mount by interfering with said at least one rib.

15. The device recited in claim 9 wherein said open second end of said cover has a reduced diameter relative to said first end of said cover and wherein an inner wall surface of said cover adjacent to said second end of said cover is tapered so that the thickness of said wall is reduced at said open second end of said cover relative to the thickness of said wall at said first end of said cover.

16. A needle protector device comprising:
    a needle subassembly having a hub and a needle extending from said hub to terminate at a tip, said hub having at least one exterior rib;
    a mount having an upper end, an interior channel extending from said upper end of said mount to terminate at a terminal end having a reduced diameter relative to a portion of said channel adjacent to said upper end of said mount, and an open lower end, wherein said needle subassembly is inserted into said channel of said mount from said upper end so that interference between said at least one rib and said interior channel causes said needle subassembly to be retained in said mount, said mount having a spring receiving aperture adjacent to said upper end;

a protective cover having an upper end coupled to said lower end of said mount, an open lower end of reduced diameter relative to said upper end of said cover, and a spring receiving aperture adjacent to said upper end of said cover; and a spring having a mount engaging extension extending axially from a first end thereof and a cover engaging extension extending axially from a second end thereof, wherein said mount engaging extension is disposed in said spring receiving aperture of said mount and said cover engaging extension is disposed in said spring receiving aperture of said cover and wherein said cover and said mount are rotated relative to one another to torsionally bias said spring in assembly.

17. The needle protector device recited in claim 16 wherein said mount and said cover include alignment features for facilitating alignment of said mount and said cover in assembly and wherein said cover and said mount are comprised of different types of polymeric materials.

18. The needle protector device recited in claim 16 wherein said interior channel of said mount has at least one protrusion extending into said channel and wherein, in assembly, said at least one protrusion prevents said needle subassembly from rotating relative to said mount by interfering with said at least one rib.

19. The needle protector device recited in claim 16 wherein said cover has a tapered inner wall with a reduced thickness at said open lower end relative to said upper end of said cover.

20. The needle protector device recited in claim 16 wherein said mount has an aperture disposed in a side thereof and an assembly ramp extending from said lower end of said mount toward said aperture and wherein said cover has a lug adapted for riding along said assembly ramp as said cover is coupled to said mount and for being positioned in said aperture once said cover and said mount are coupled.

* * * * *

UNITED STATES PATENT AND TRADEMARK OFFICE
CERTIFICATE OF CORRECTION

PATENT NO. : 5,795,336
DATED : August 18, 1998
INVENTOR(S) : Romano, et al.

It is certified that error appears in the above-identified patent and that said Letters Patent is hereby corrected as shown below:

| Column | Line(s) | | |
|---|---|---|---|
| 1 | 7 | 08/1387,676 | 08/387,676 |
| 1 | 12 | 016285 | 08/016,285 |

Signed and Sealed this

Twenty-third Day of February, 1999

Attest:

Q. TODD DICKINSON

*Attesting Officer*    *Acting Commissioner of Patents and Trademarks*